(12) United States Patent
Holmes et al.

(10) Patent No.: US 10,345,272 B2
(45) Date of Patent: Jul. 9, 2019

(54) AUTOMATED CALIBRATION OF NON-DESTRUCTIVE TESTING EQUIPMENT

(71) Applicant: The Boeing Company, Chicago, IL (US)

(72) Inventors: Tyler M. Holmes, Seattle, WA (US); Jeffrey R. Kollgaard, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 342 days.

(21) Appl. No.: 14/797,462

(22) Filed: Jul. 13, 2015

(65) Prior Publication Data

US 2017/0016862 A1    Jan. 19, 2017

(51) Int. Cl.
| | |
|---|---|
| *G01N 29/30* | (2006.01) |
| *G01N 29/06* | (2006.01) |
| *G01N 29/04* | (2006.01) |
| *G01N 29/44* | (2006.01) |

(52) U.S. Cl.
CPC ............. *G01N 29/30* (2013.01); *G01N 29/04* (2013.01); *G01N 29/0654* (2013.01); *G01N 29/4427* (2013.01); *G01N 29/4472* (2013.01)

(58) Field of Classification Search
CPC .... G01N 29/30; G01N 29/04; G01N 29/4427; G01N 29/4472
USPC .............................................. 702/103; 73/592
See application file for complete search history.

(56) References Cited

U.S. PATENT DOCUMENTS

| | | | |
|---|---|---|---|
| 4,462,082 A | | 7/1984 | Thiele et al. |
| 5,902,935 A | * | 5/1999 | Georgeson ......... G01N 29/2412 73/801 |
| 7,562,576 B2 | | 7/2009 | Fetzer et al. |
| 7,800,363 B2 | | 9/2010 | Bousquet et al. |
| 8,336,365 B2 | | 12/2012 | Deangelo et al. |
| 8,522,615 B1 | | 9/2013 | Brady et al. |

(Continued)

FOREIGN PATENT DOCUMENTS

| | | | |
|---|---|---|---|
| EP | 2728548 A2 | 5/2014 | |
| EP | 2752657 A2 | 7/2014 | |

OTHER PUBLICATIONS

Extended European Search Report dated Mar. 17, 2017 in European Patent Application No. 16168164.8 (European counterpart of the instant U.S. patent Application).

*Primary Examiner* — Dzung Tran (74) *Attorney, Agent, or Firm* — Ostrager Chong Flaherty & Broitman, P.C (57) ABSTRACT

A method for auto-calibrating a non-destructive testing instrument. In accordance with some embodiments, the method comprises: (a) determining a first set of coordinates in a test object coordinate system of the test object, the first coordinates representing a target position on a surface of the test object; (b) storing a calibration file in a memory of the non-destructive testing instrument, the calibration file containing calibration data which is a function of structural data representing a three-dimensional structure of the test object in an area containing the target position; (c) calibrating the non-destructive testing instrument using the calibration data in the calibration file; and (d) interrogating the target position using the calibrated non-destructive testing instrument.

15 Claims, 7 Drawing Sheets

(56) References Cited

U.S. PATENT DOCUMENTS

| | | | |
|---|---|---|---|
| 2009/0150095 A1* | 6/2009 | Wickersham, Jr. | C22C 27/02 702/39 |
| 2010/0107725 A1* | 5/2010 | Iizuka | G01N 29/11 73/1.82 |
| 2011/0283798 A1* | 11/2011 | Yamano | G01N 29/043 73/632 |
| 2012/0327187 A1* | 12/2012 | Troy | G01N 29/0654 348/46 |
| 2014/0238136 A1 | 8/2014 | Ten Grotenhuis et al. | |

* cited by examiner

AUTOMATED CALIBRATION OF NON-DESTRUCTIVE TESTING EQUIPMENT

BACKGROUND

This disclosure generally relates to systems and methods for non-destructive testing (NDT) of manufactured articles, and in particular, to methods for calibrating NDT instruments.

Non-destructive testing and results analysis of manufactured articles (such as airplane) preferably includes participation by specially trained NDT inspectors. Generally the trained inspector will be called out to the inspection site for the purpose of inspecting the part. During the set-up procedure, typically the trained inspector will calibrate the NDT instrument for the area of the part to be inspected. This can be a time-consuming process. The process can be more difficult for set-up technicians who are not trained NDT inspectors.

It would be advantageous to provide an automated method for calibrating an NDT instrument that does not require the presence of a trained NDT inspector at the inspection site and may reduce the time taken to calibrate the equipment.

SUMMARY

The subject matter disclosed in detail below solves the problem of requiring a trained NDT inspector to perform equipment calibrations by automating the process through the use of three-dimensional (3-D) model data. Since the calibration will be automated, it is possible to have a non-NDT person perform a basic inspection. This reduces lead time, since there will be no need to wait for an off-site trained NDT inspector to arrive at the inspection site, and time is also saved through the automation of the calibration process. The automated calibration method disclosed herein also reduces the potential for human error.

One aspect of the subject matter disclosed in detail below is a method for auto-calibrating a non-destructive testing instrument, comprising: (a) determining a first set of coordinates in a test object coordinate system of the test object, the first coordinates representing a target position on a surface of the test object; (b) storing a calibration file in a memory of the non-destructive testing instrument, the calibration file containing calibration data which is a function of structural data representing a three-dimensional structure of the test object in an area containing the target position; and (c) calibrating the non-destructive testing instrument using the calibration data in the calibration file. This method may further comprise interrogating the target position using the calibrated non-destructive testing instrument.

In accordance with some embodiments, the method described in the preceding paragraph may further comprise: obtaining structural data representing a three-dimensional structure of the test object in an area containing the target position; and generating the calibration file based on the target position and the structural data. In accordance with other embodiments, the method described in the preceding paragraph may further comprise: obtaining structural data representing a three-dimensional structure of the test object; and displaying a graphical representation of the structural data on a display screen of the non-destructive testing instrument, wherein step (a) comprises interacting with the display screen to select a location on the display screen corresponding to the target position on the surface of the test object. In accordance with further embodiments, the method described in the preceding paragraph may further comprise: (d) locating a local positioning system relative to the test object; (e) generating a transformation matrix for transforming coordinates in a local positioning system coordinate system of the local positioning system into coordinates in the test object coordinate system of the test object; and (f) determining a second set of coordinates representing the target position on the surface of the test object in the coordinate system of the local positioning system, wherein step (a) comprises transforming the second set of coordinates into the first set of coordinates using the transformation matrix. In accordance with other embodiments, the method described in the preceding paragraph may further comprise: (d) attaching a position sensor to the non-destructive testing instrument; and (e) moving the non-destructive testing instrument to a location at which the position sensor is aligned with the target position, wherein step (a) comprises calculating the first set of coordinates based on an output of the position sensor while the position sensor is aligned with the target position.

The structural data used to generate or retrieve the calibration file may comprise information concerning one or more of the following structural features of the test object at or in the area containing the target position: physical dimensions, material characteristics, fastener locations, structural anomalies, an alteration or a repair to the test object, average paint thickness, hidden stringers, electromagnetic effects (EME) protection layers and other features that may not be accounted for in a general inspection.

Another aspect of the subject matter disclosed in detail below is a method for auto-calibrating a non-destructive testing instrument, comprising: (a) determining a first set of coordinates in a test object coordinate system of the test object, the first coordinates representing a target position on a surface of the test object; (b) obtaining structural data representing a three-dimensional structure of the test object in an area containing the target position; (c) generating a calibration file containing calibration data which is a function of the structural data obtained in step (b); and (d) calibrating the non-destructive testing instrument using the calibration data in the calibration file. This method may further comprise: (e) locating a local positioning system relative to the test object; (f) generating a transformation matrix for transforming coordinates in a local positioning system coordinate system of the local positioning system into coordinates in the test object coordinate system of the test object; and (g) determining a second set of coordinates representing the target position on the surface of the test object in the coordinate system of the local positioning system, wherein step (a) comprises transforming the second set of coordinates into the first set of coordinates using the transformation matrix.

A further aspect of the subject matter disclosed in detail below is a method for auto-calibrating a non-destructive testing instrument, comprising: locating a local positioning system coordinate system of a local positioning system relative to a test object coordinate system of a test object; locating a feature on the test object relative to the local positioning system coordinate system; converting the location of the feature in the local positioning system coordinate system to a location of the feature in the test object coordinate system; retrieving structural data from a database based on the location of the feature in the test object coordinate system, the structural data representing a structure of the test object in an area containing the location of the feature; storing a calibration file in a memory of the non-destructive testing instrument, the calibration file containing data which is a function of the retrieved structural data; and calibrating the non-destructive testing instrument using data in the stored calibration file. This method may further comprise generating the calibration file or retrieving the calibration file from a database.

Yet another aspect is a system comprising a non-destructive testing instrument and a computer system programmed to perform the following operations: (a) determining a set of coordinates in a test object coordinate system of the test object, the coordinates representing a target position on a surface of the test object; (b) obtaining structural data representing a three-dimensional structure of the test object in an area containing the target position; (c) generating the calibration file based on the target position and the structural data; (d) storing the calibration file in a memory, the calibration file containing calibration data which is a function of the structural data; and (e) calibrating the non-destructive testing instrument using the calibration data in the calibration file.

Other aspects of automated methods for calibrating NDT instruments are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to the drawings which illustrate at least some of the above-described and other aspects.

DETAILED DESCRIPTION

Various auto-calibration methods will now be described with reference to ultrasonic NDT instruments for the purpose of illustration only. It should be appreciated that other types of NDT instruments can be auto-calibrated in similar ways. One type of ultrasonic NDT instrument will now be described in detail to provide context and terminology for the calibration-related improvements disclosed herein.

Figure 1:
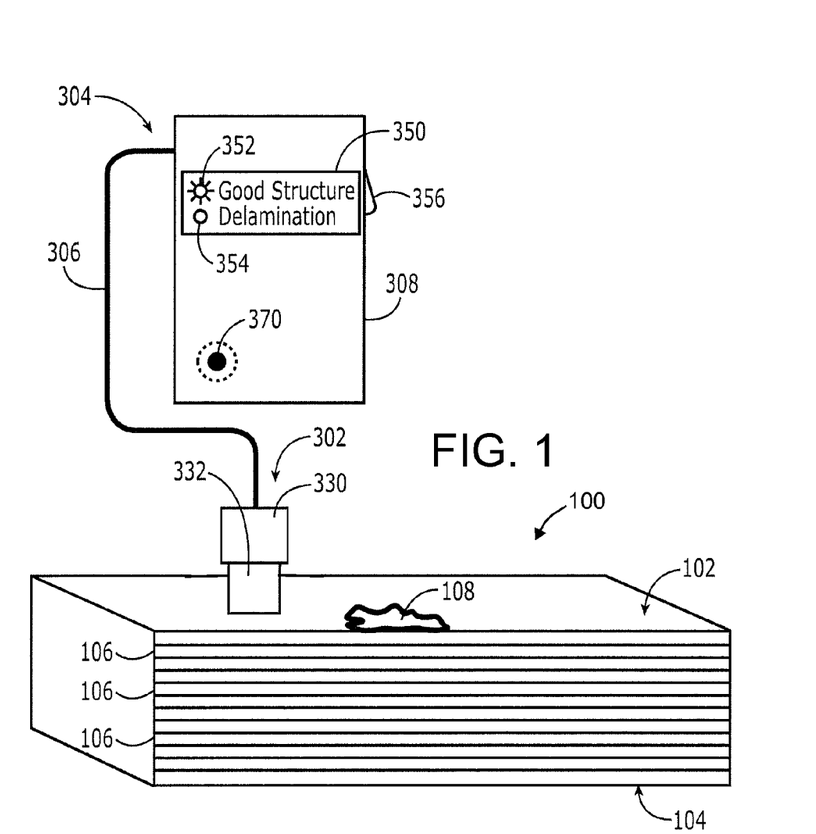
FIG. 1 is a diagram depicting an NDT instrument having an ultrasonic transducer acoustically coupled to a laminate structure to be inspected.

FIG. 1 illustrates some components of one type of NDT instrument. This NDT instrument comprises an ultrasonic transducer device 302 and an electronic device 304 having a housing 308, a display 350, a power switch 356, and a hidden calibration activator 370. The display 350 comprises a first indicator 352 for indicating that no damage within an inspected structure was detected by the apparatus, and a second indicator 354 for indicating that damage may be present. The ultrasonic transducer device 302 comprises an ultrasonic transducer 330 and an acoustic coupling element 332 attached thereto and disposed between the ultrasonic transducer 330 and a surface 102 of an exemplary laminate structure 100 under inspection. An activator assembly 362 is attached to the ultrasonic transducer device 302.

During the inspection procedure, the ultrasonic transducer device 302 is typically pressed against a surface 102 of the laminate structure 100 and one of the first and second indicators 352, 354 is automatically activated to indicate whether, respectively, the laminate structure 100 is likely in good condition or likely damaged. In a pulse-echo mode, the ultrasonic transducer 330 sends an ultrasonic pulse into the inspected structure and then generates an electrical signal when an ultrasonic echo signal returns from that structure. Outgoing ultrasonic pulses traveling through a structure tend to reflect from surfaces, edges, and other discontinuities such as damages in the structure. A returning ultrasonic echo signal can include multiple time-distributed return pulses. Returning ultrasonic echo signals are referred to herein as "echo profiles". Typical echo profiles include return pulses reflected from surfaces and edges that are expected and return pulses reflected from damage that deserves investigation and repair. The electrical signal generated by the ultrasonic transducer 330 conveys amplitude and time data corresponding to the amplitudes and arrival times of return pulses within the echo profile. The electronic device 304 activates the ultrasonic transducer 330 to send outgoing ultrasonic pulses and receives signals generated by the ultrasonic transducer 330 by way of one or more conductive cables 306.

Figure 2:
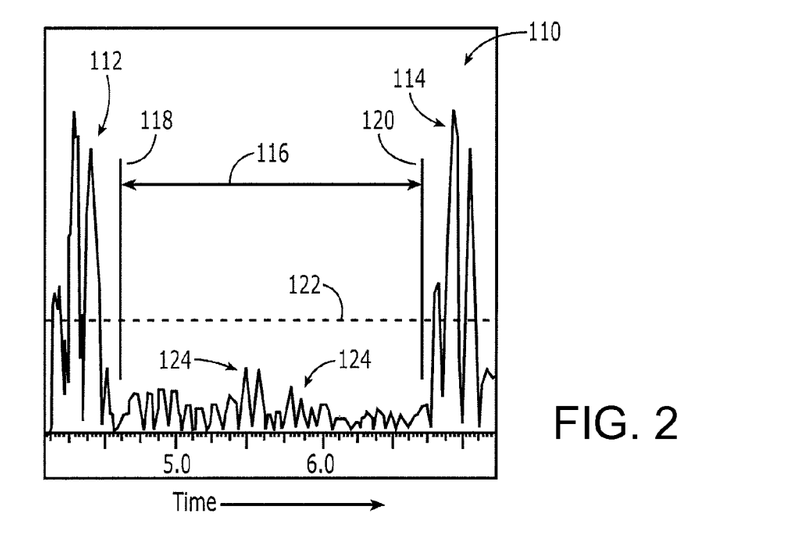
FIG. 2 is a graph of an echo profile generated by the ultrasonic transducer device depicted in FIG. 2.

The ultrasonic transducer device 302 shown in FIG. 1 emits one or more ultrasonic pulses into the laminate structure 100 and detects the echo profile 110 shown in FIG. 2. In the scenario depicted in FIG. 2, the ultrasonic transducer 330 is disposed along the surface 102 at a location where no flaws are present in the underlying structure. Thus, the echo profile 110 detected by the ultrasonic NDT instrument is indicative of a defect-free structure.

The laminate structure 100 depicted in FIG. 1 can be part of many different types of structures, such as those found in airplanes, automobiles and other vehicles, or any other structure that can benefit from a light, yet strong material. The laminate structure 100 has a front surface 102 and a back surface 104 and is composed of multiple individual laminate sheets 106. The laminate sheets are joined together by a bonding material. In the course of normal use, laminate materials are subject to accidental damage. In some instances the resultant damage will be small while in other instances the damage may be moderate to severe. For example, the laminate structure 100 in FIG. 1 is depicted as being so lightly damaged that a marking visibly apparent at an impact site 108 is merely superficial and not a threat to the integrity of the structure.

The electrical waveform 110 shown in FIG. 2 represents the electrical signal generated by the ultrasonic transducer 330 as graphically displayed on an instrument such as an oscilloscope (not shown in FIGS. 1 and 2). Electrical fluctuations having various amplitudes rise vertically above the "Time" axis such that early fluctuation events are shown on the left and subsequent events are represented by considering the waveform from left to right. Thus the electrical signals 112 depicted in FIG. 2 are generated by the ultrasonic transducer 330 before the electrical signals 114. Although the groups of electrical signals 112 and 114 are composed of high-frequency oscillations, they will be referred to hereinafter as "pulses". Furthermore, the electrical waveform 110 is intended to represent multiple time-ordered ultrasonic return pulses that echo from features of the ultrasonically inspected structure. Thus, the electrical waveform 110 will be hereinafter referred to as "echo profile 110" and the electrical signals 112 and 114 will be hereinafter referred to as "return pulses 112 and 114". The echo profile 110 includes the return pulse 112 that returned from the front surface 102 of the laminated structure 100 as an echo after an outgoing ultrasonic pulse was sent toward the structure, through the coupling element 332, by the ultrasonic transducer 330. The echo profile 110 also includes the return pulse 114 that similarly returned as an echo from the back surface 104. Outgoing pulses are not illustrated as portions of echo profiles herein but should be understood to have occurred at times preceding the front-surface return pulse in FIG. 2.

The acoustic coupling element 332 provides dry coupling between the ultrasonic transducer 330 and the interrogated laminate structure 100 and serves as a delay line in that it imposes a delay time between outgoing pulses at the ultrasonic transducer 330 and return pulses according to the length of the acoustic coupling element 332 and according to the speed at which ultrasound waves propagate within the acoustic coupling element 332. If the ultrasonic transducer 330 were coupled to a surface without a delay line, an outgoing pulse would be followed closely in time by a return pulse from the surface. In such a situation, the outgoing pulse and the front-surface return pulse are difficult to separately distinguish and illustrate. However, the acoustic coupling element 332 depicted in FIG. 1 spaces the ultrasonic transducer 330 from the front surface 102 of the laminated structure 100. Thus, the time of flight (TOF) of the front-surface return pulse 112 includes at least the time for an outgoing pulse to propagate from the ultrasonic transducer 330 to the contact face of the acoustic coupling element 332 and back to the ultrasonic transducer 330. Thus, the outgoing pulse would have occurred prior to the time range depicted in FIG. 2. It should be understood that, in this context, the TOF of a return pulse is generally defined as the time elapsed between the time of a transducer's sending of an outgoing pulse and the time of the transducer's receipt of the return pulse. Thus, the "Time" axis of FIG. 2 can be considered a portion of a relative TOF axis, wherein the origin of the axis, as defined by the time of an outgoing pulse, is not shown.

Still referring to FIG. 2, a time-gated portion 116 (indicated by a horizontal double-headed arrow) of the echo profile is disposed between a gate-initiating time 118 and a gate-closing time 120 (indicated by vertical lines). The initiating and closing times are predetermined according to a calibrating procedure discussed in more detail below. Ultrasonic waves tend to echo from structural discontinuities such as surfaces and flaws including delaminations, fissures, voids, and contaminants. In FIG. 2, the time-gated portion 116 of the echo profile 110 is free of significant return pulses because such flaws are not present in the laminate structure 100 depicted in FIG. 1. More particularly, such flaws are not present in the portion of the laminate structure 100 under the ultrasonic transducer device 302. In order for the ultrasonic NDT instrument to distinguish significant return pulses that discriminate structural flaws from insignificant noise and minor fluctuations 124, a threshold 122 (indicated by a horizontal dashed line) may also be predetermined or established according to the calibrating procedure described below. In FIG. 2, no return pluses having amplitudes exceeding the threshold 122 are within the time-gated portion 116 of the echo profile 110. According to the configuration and calibration of the electronic device 304 depicted in FIG. 1, the indicator 352 is automatically activated to indicate no damage has been detected by the ultrasonic transducer device 320 despite the presence of minor fluctuations 124. In contrast, in cases when a return pulse is present within the time gate 116, which pulse has a magnitude exceeding the threshold 122, the indicator 354 is activated in FIG. 1 to alert an operator to the likely presence of hidden damage in the laminate structure 100.

The time-gate initiating and closing times 118 and 120 are established by choice to closely follow and precede front-surface and back-surface return pulses. This configuration choice for the ultrasonic NDT instrument depicted in FIG. 1 serves to detect return pulses, within an echo profile 110, received from between the front and back surfaces. However, depth is correlated with the time of flight (TOF) measured between the dispatch of an outgoing pulse and the receipt of a return pulse. Once a time gate is established, relative quiescence and relative return-pulse activity, with respect to the established threshold, within the time gate cause automatic activations of the indicators 352 and 354, respectively. This is true without regard to the ongoing presence of front and back surface return pulses. Thus, in a more general sense, the initiating and closing times can be established so that the ultrasonic NDT instrument informs an operator of the likely presence or absence of return pulses from any chosen depth range. Any desired depth range, defined between a first depth and a second depth, can be chosen for inspection by establishing or predetermining both a gate-initiating time corresponding to the first depth and a gate-closing time corresponding to the second depth.

The ultrasonic NDT instrument depicted in FIG. 1 can measure thickness, depth or distance by very precisely timing echoes. In order to turn these time measurements into distance measurements, the NDT instrument is calibrated with the speed of sound in the laminate structure (or other test material) as well as any necessary zero offset. This process is commonly referred to as velocity/zero calibration. The accuracy of any ultrasonic thickness, depth or distance measurement is dependent on the accuracy of the calibration. Calibrations for different materials and transducers can be stored and retrieved.

In a typical velocity calibration, the ultrasonic NDT instrument measures the speed of sound in a reference sample of the test material and then stores that value for use in calculating thickness from measured time intervals. In a typical zero calibration, the ultrasonic NDT instrument measures a material sample of known thickness and then calculates a zero offset value that compensates for the portion of the total pulse transit time that represents factors other than the actual sound path in the test material.

For example, in a typical procedure for calibrating an ultrasonic NDT instrument, the following steps are performed. If the equipment includes an X-Y scanner, the inspection distance increments are set. Then the pulser frequency is set to the frequency of the transducer. If a receiver frequency can be adjusted, it is set to broadband. Then the material velocity is set. If the probe is a linear array, the following adjustments are made: set the focus distance;

set the number of firing elements; set the first element to 1 and the last element to the number of elements in the array; and make sure that the linear array has a constant back surface signal from all of the elements. Then an A-scan screen range is set to no less than the maximum structure thickness in the inspection area. Next, three gates are made on the A-scan display. The three gates are an interface (i.e., front surface) gate, a second gate that monitors the depth (time-of-flight), and a third gate that monitors the height of the back surface signal. Then a reference standard may be used to set the Time-Compensated Gain (TCG). Typically the TCG is adjusted for a back surface signal of 80% (±10%) of full screen height. This typical calibration process may take an inordinate amount of time to carry out even for a skilled NDT inspector.

It would be advantageous to provide an automated method for calibrating an NDT instrument that does not require the presence of a trained NDT inspector at the inspection site and may reduce the time taken to calibrate the equipment. Illustrative embodiments of automated methods are described in some detail below. However, not all features of an actual implementation are described in this specification. A person skilled in the art will appreciate that in the development of any such actual embodiment, numerous implementation-specific decisions are made to achieve the developer's specific goals, such as compliance with system-related constraints, which will vary from one implementation to another. Moreover, it will be appreciated that such a development effort might be complex and time-consuming, but would nevertheless be a routine undertaking for those of ordinary skill in the art having the benefit of this disclosure.

The automated calibration method can entail, for example, establishing the speed of propagation of ultrasonic pulses in the inspected material in order to correlate TOF measurements with material depths, and selecting time and depth axes ranges and time-gate settings for A-scan, B-scan, and C-scan windows. Depth is derived from the time of flight (TOF) measured between the dispatch of an ultrasonic pulse into a structure and the return of an echo pulse. If the speed of propagation of ultrasonic pulses is known for a particular inspected material, the vertical axis of the scan window can be calibrated toward particular linear depth dimensions according to the TOF of each echo pulse.

The methodology disclosed herein automates the calibration of NDT instruments through the use of three-dimensional (3-D) CAD data representing a 3-D model of the structure to be inspected. By basing calibration on a CAD model, it is possible to pull more data into location-specific inspections. CAD model data (i.e., also referred to herein as "structural data") may comprise information concerning one or more of the following structural features of the test object at or in the area containing the target position: physical dimensions, material characteristics, fastener locations, structural anomalies, an alteration or a repair to the test object, average paint thickness, hidden stringers, EME protection layers and other features that may not be accounted for in a general inspection.

Figure 3:
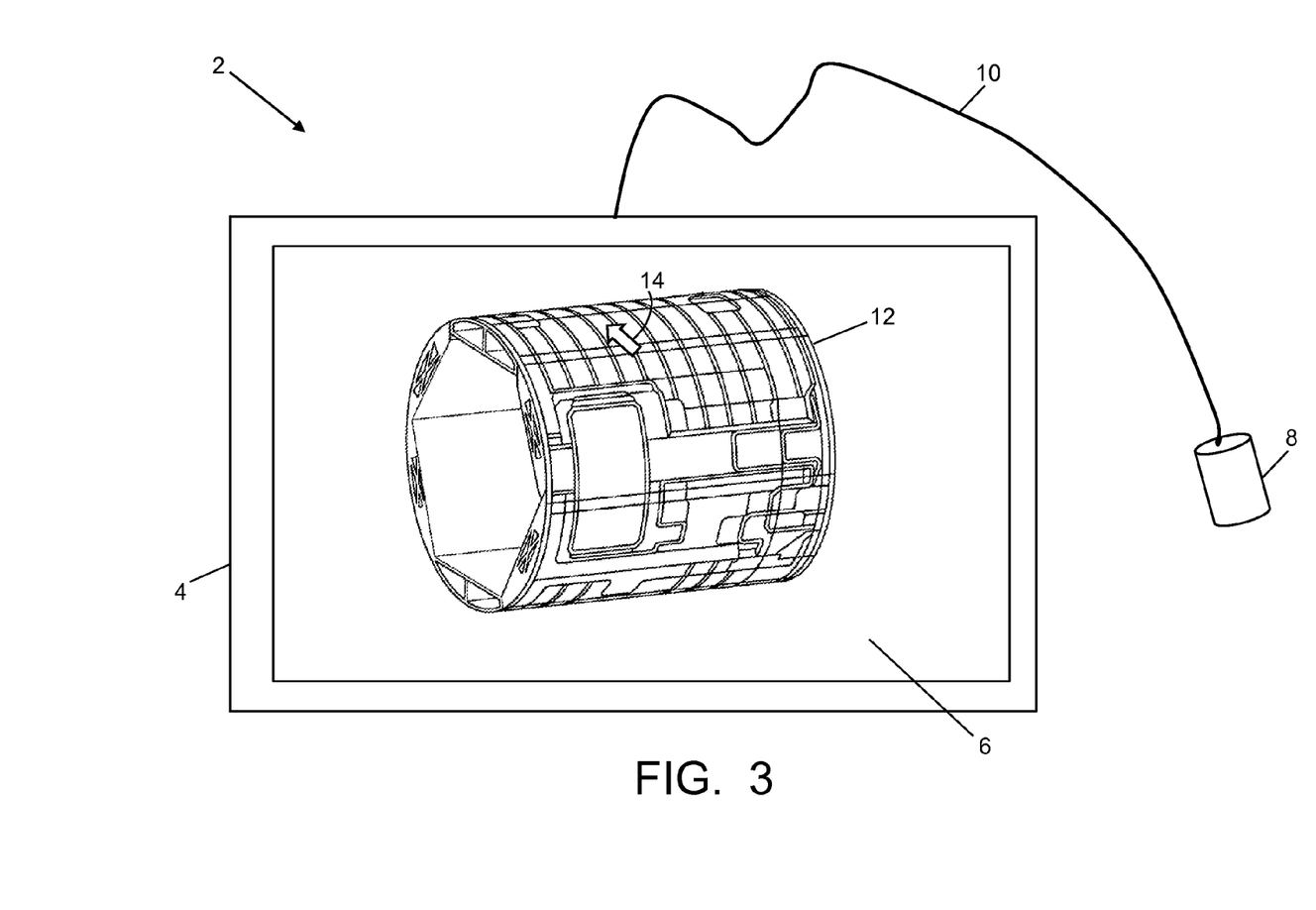
FIG. 3 is a diagram representing a front view of an NDT instrument loaded with a CAD model of a part to be inspected.

In accordance with some embodiments, an NDT instrument is loaded with a CAD model of a part or a portion of a part to be inspected. The NDT instrument 2 depicted in FIG. 3 comprises a housing 4, a display screen 6, a probe 8 and an electrical cable 10 connecting the probe 8 to a processor or computer (not shown) disposed inside the housing 4. An image 12 produced from a CAD model of a barrel-shaped airplane fuselage section is presented on the display screen 6. The 3-D model data loaded into memory inside the NDT instrument 2 comprises relevant thicknesses and material data for the part being inspected, which information can be used (along with other relevant information as described above) to automatically calibrate the NDT instrument. More specifically, the inspector can click on a pixel on the display screen 6 at a position indicated by a cursor 14 in FIG. 3. In response to this selection, relevant thicknesses and material data for a corresponding area on the surface of the fuselage section to be inspected will be retrieved from the file containing the DAD model. An appropriate calibration file can then be automatically created or retrieved and then loaded into the NDT instrument 2.

Figure 4:
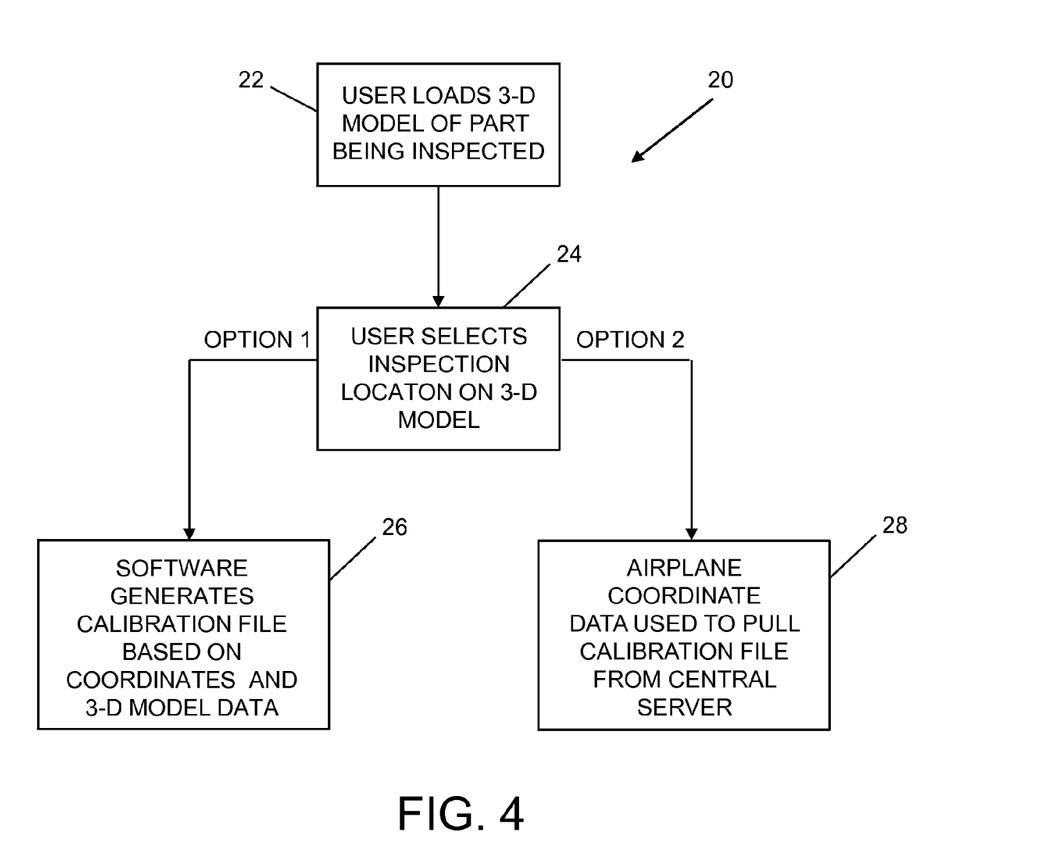
FIG. 4 is a flowchart identifying steps of a method for calibrating an NDT instrument involving manual location selection in accordance with alternative embodiments.

FIG. 4 is a flowchart identifying steps of a method 20 for calibrating the NDT instrument 2 in accordance with some embodiments, which method involves manual location selection. Prior to the inspection procedure, an inspector loads a CAD file containing a 3-D model for the part/area to be inspected into the NDT instrument (step 22). An image representing the 3-D model of the structure to be inspected is displayed as a graphical user interface on the display screen. The inspector then manually selects the target position by clicking on the image 12 of the 3-D model at a corresponding location indicated by the cursor 14 in FIG. 3 (step 24). The aforementioned processor or computer inside the NDT instrument 2 is programmed with software that will pull the thickness and other material data for the selected location from the CAD file and either: (a) generate a calibration file on the fly based on the 3-D model data (step 26); or (b) pull a calibration file from a calibration file server (step 28). The NDT instrument can communicate with the calibration file server by means of a network (e.g., the Internet). It would also be possible to create the calibration file by a separate computer using software and 3-D model data and then transmitting the calibration file to the NDT instrument.

Figure 5:
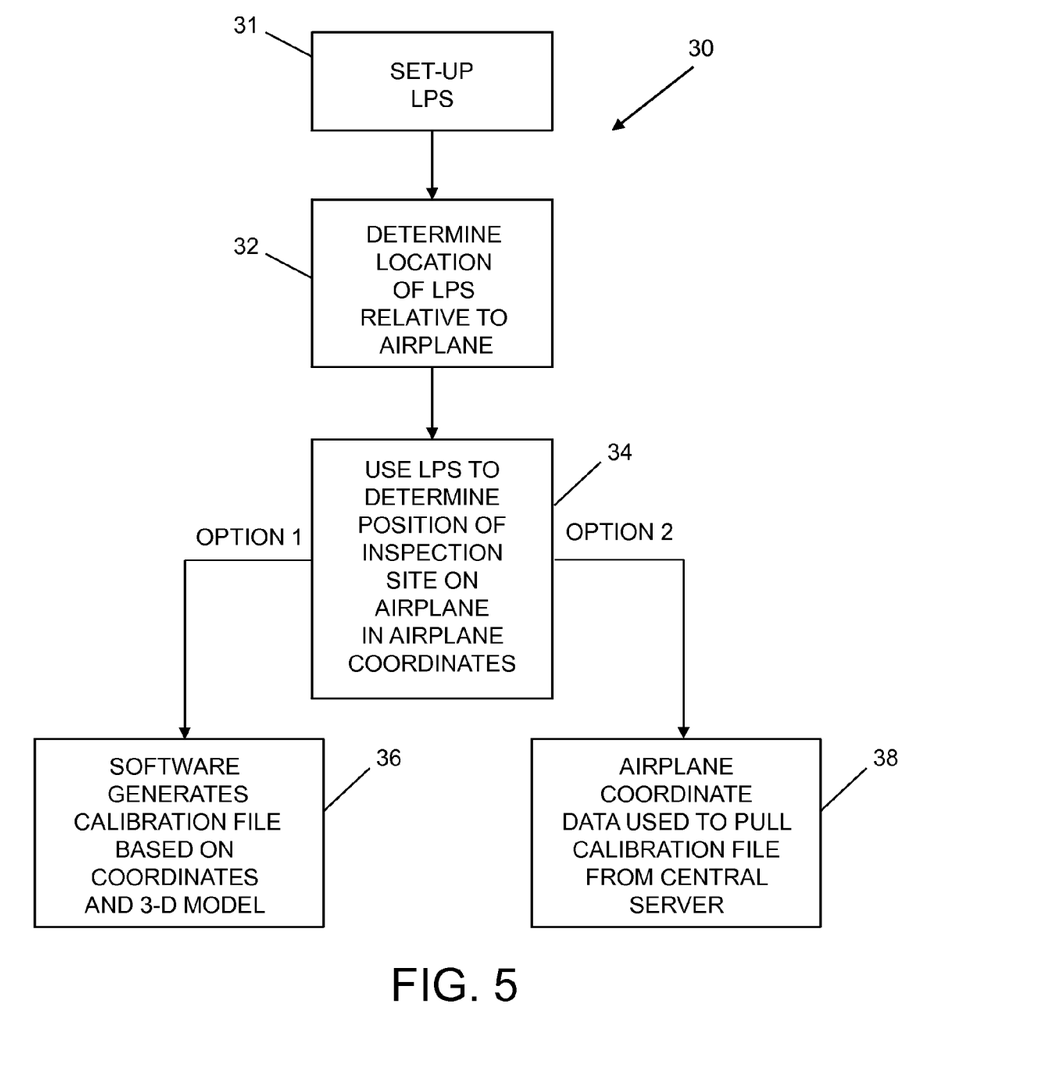
FIG. 5 is a flowchart identifying steps of a method for calibrating an NDT instrument involving automatic location determination in accordance with alternative embodiments.

In accordance with other embodiments, a local positioning system (a.k.a. a laser tracker) can be used to automatically determine the position of an inspection site in an airplane-centered coordinate system and then automatically calibrate an NDT instrument based on the airplane coordinates of the inspection site. FIG. 5 is a flowchart identifying steps of a method 30 for calibrating an NDT instrument involving automatic location determination using a local positioning system (LPS) of a type which will be described in detail below with reference to FIG. 6. Prior to the inspection procedure, an inspector sets up the LPS so that the inspection site on the airplane is within the field of view of a camera of the LPS (step 31). Then the inspector uses the LPS to determine the location (i.e., position and orientation) of the LPS relative to the airplane (step 32). The inspector then directs a laser range finder of the LPS so that a laser beam impinges on the inspection site on the surface of the airplane. (Alternatively, a computer with image processing software could be used to detect damage on the surface of the airplane and then automatically direct the LPS so that the laser beam impinges on the damage site.) Based on the measured distance from the laser range finder to the inspection site, a computer of the LPS can determine the position of the inspection site on the airplane in airplane coordinates (step 34). That information can be sent to a CAD database server which is programmed to retrieve a CAD file containing data regarding the structure in the locality of the inspection site. A processor or computer (inside or not inside the NDT instrument 2) can be programmed with software that will pull the thickness and other material data for the selected location from the CAD file and either: (a) generate a calibration file on the fly based on the 3-D model data (step 36); or (b) pull a calibration file from a calibration file server (step 38). All of the computers mentioned in this paragraph can be interconnected by means of a network (e.g., the Internet) to form a computer system. In cases where the calibration file is created by a separate computer using software and the 3-D model data, the separate computer will transmit the calibration file to the NDT instrument.

In accordance with some embodiments, the method for auto-calibrating the NDT instrument 2 using a local positioning system comprises: locating a local positioning system coordinate system of a local positioning system relative to a test object coordinate system of a test object; locating a feature on the test object relative to the local positioning system coordinate system; converting the location of the feature in the local positioning system coordinate system to a location of the feature in the test object coordinate system; retrieving structural data from a database based on the location of the feature in the test object coordinate system, the structural data representing a structure of the test object in an area containing the location of the feature; storing a calibration file in a memory of the NDT instrument 2, the calibration file containing data which is a function of the retrieved structural data; and calibrating the NDT instrument 2 using data in the stored calibration file.

Figure 6:
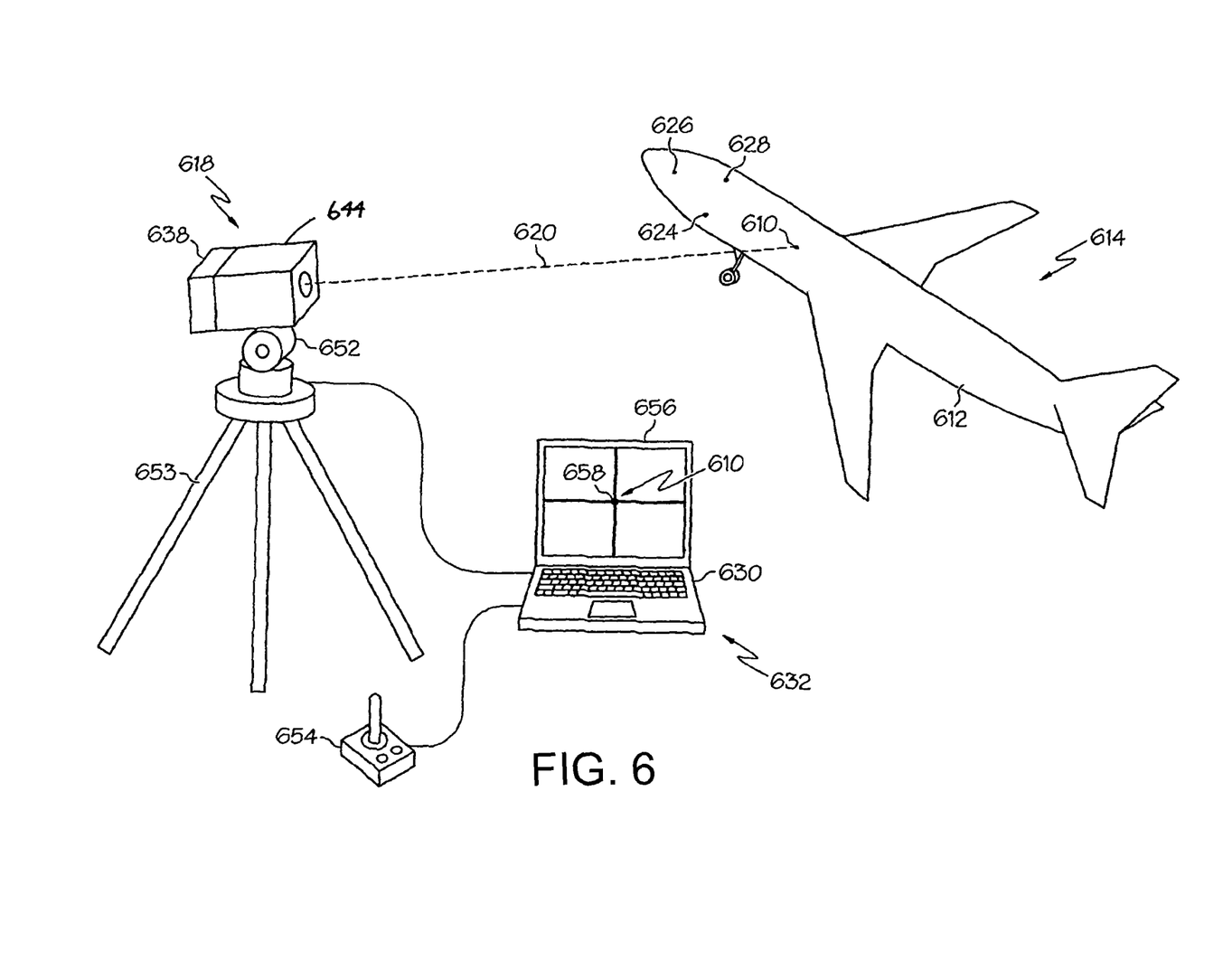
FIG. 6 is a diagram representing an isometric view of a local positioning system directing a beam of light at a location on the surface of an airplane.

One example of a local positioning system capable of determining a position of a point of interest 610 on a surface 612 of a test object 614 (in this example, an airplane) is depicted in FIG. 6. This local positioning system comprises a pointing instrument 618 having an aim point axis 620 and an instrument coordinate system. In FIG. 6, the aim point axis 620 is represented by a dashed line which extends from the lens of video camera 644 and intersects a point of interest 610 on the surface 612 of the test object 614. In the embodiment shown in FIG. 6, the pointing instrument 618 includes a pan-tilt unit 652 which is supported by a tripod 653. The instrument coordinate system may be the fixed coordinate system of the tripod 653 (or other platform on which the pan-tilt unit is attached). The test object 614 has its own coordinate system different than the instrument coordinate system.

The pointing instrument 618 further comprises a video camera 644 equipped with a laser range finder 638. The video camera 644 is mounted on the pan-tilt unit 652 to allow the video camera 644 and laser range finder 638 to be rotated in pan and tilt. The pointing instrument 618 may be operated by a computer 632 (e.g., a personal computer). The computer 632 received signals from a joy stick input device 654 and sends signals to a display monitor 656. In one modification, the computer 632 is programmed to control the pan-tilt unit 652 through the joy stick input device 654, to display a field of view of the video camera 644 on the display monitor 656, to overlay a representation 658 (such as the center of cross-hairs) of the aim point axis 620 on the display, and to measure the pan and tilt angles (and distance for the calibration matrix) when a user of the joy stick input device 654 aligns the representation 658 of the aim point axis 620 on the monitor 656 with the point of interest 610 and indicates such alignment to the computer 632. A direction vector that describes the orientation of the aim point axis 620 relative to the instrument coordinate system can be determined from the azimuth and elevation angles, as well as the position of the center of a crosshair marker in the optical field when the video camera 644 is aimed at the point of interest 610.

The video camera 644 and the pan-tilt mechanism 652 may be operated in accordance with programming stored in computer memory 630. The computer 632 communicates with video camera 644 and pan-tilt mechanism 652 through a video/control cable 642. Alternatively, the computer 632 may communicate with video camera 644 and pan-tilt mechanism 652 through a wireless communication pathway (not shown). Control of the pan-tilt mechanism 652 and, therefore, the orientation of the video camera 644 may be controlled using the keyboard of computer 632, a mouse (not shown), a track ball (not shown) or another input device.

In addition, three-dimensional localization software is loaded into computer memory 630 of the computer 632. For example, the three-dimensional localization software may be of a type that uses multiple calibration points 624, 626 and 628 on the surface 612 of test object 614 to define the location (position and orientation) of video camera 644 relative to test object 614. In some applications, the three-dimensional localization software may utilize a minimum of three calibration points 624, 626 and 628 on the surface 612 of test object 614, in combination with pan and tilt data from the pan-tilt mechanism 652, to define the relative position and orientation of the video camera 644 with respect to the local coordinate system of the test object 614. The calibration points may be visible features of known position in the local coordinate system of the test object 614 as determined from a three-dimensional model database of feature positions (e.g., a CAD model) or other measurement technique. The calibration points may be used in coordination with the azimuth and elevation angles from the pan-tilt mechanism 652 to solve for the camera position and orientation relative to the test object 614. More specifically, the three-dimensional localization software loaded onto the computer 632 can determine the position and orientation of the video camera 644 with respect to the test object 614 and generate a camera pose transformation matrix.

In accordance with one exemplary method, an orientation of the aim point axis 620 is measured with respect to the instrument coordinate system when the aim point axis 620 is in turn aligned with each of three calibration points 624, 626 and 628 on the surface 612 of test object 614, wherein positions of the three calibration points 624, 626 and 628 in the test object coordinate system are known. This method also includes measuring a distance (i.e., range) substantially along the aim point axis 620 from the instrument 618 to each of the three calibration points 624, 626 and 628. A calibration matrix is then calculated which transforms a position defined in the instrument coordinate system to a position defined in the test object coordinate system using at least the measured orientation and distance in the instrument coordinate system corresponding to the three calibration points 624, 626 and 628 and the known positions of the three calibration points 624, 626 and 628 in the test object coordinate system. The coordinates of these known positions are included in CAD model data representing the structure being inspected.

Once the position and orientation of the video camera 644 with respect to the test object 614 have been determined, the computer 632 may be operated to rotate and zoom the optical image field of the video camera 644 to a desired point of interest 610 of unknown position on the surface 612 of test object 614, which may be a target position on a surface of an airplane, for example. At this position of the direction vector 620, the orientation of the video camera 644 (which may include the respective angles of the video camera 644 along the azimuth and elevation axes) may be recorded. The camera pan data (angle of rotation of video camera 644 about the azimuth axis) and tilt data (angle of rotation of video camera 644 with respect to the elevation axis) may be used in conjunction with the calculated position and orientation of video camera 644 to determine the (X,Y,Z) position of any point of interest (such as the target position on the skin of an airplane) in the coordinate system of the test object 614. The surface position of the point of interest 610 may be determined from three-dimensional data in the CAD model database.

The CAD model database also includes information concerning the structure underlying the surface 612 of the test object 614 in the area surrounding the point of interest 610, which information can be used to automatically calibrate the NDT instrument that will be used to inspect that area.

In accordance with alternative embodiments, the position of the inspection site in airplane coordinates could be automatically determined using a position sensor—such as an inertial, local GPS, ultrasonic, optical, or magnetic sensor—mounted on the inspection head, i.e., probe, of the NDT instrument. The position sensor can be triangulated relative to two or three "golden rivet" or reference positions on the airplane. Those physical reference points (rivets, corners, ports, etc.) would be known in the airplane coordinate system. This would be a more involved set-up than the LPS, but would be another way to determine the position of the region of interest (i.e., the site to be inspected) on the airplane in airplane coordinates.

In accordance with some embodiments, the method for auto-calibrating the NDT instrument 2 using a position sensor comprises: attaching a position sensor to the NDT instrument 2; moving the NDT instrument until the position sensor is aligned with a target position on a surface of the test object; calculating a set of coordinates of the target position in a test object coordinate system of the test object based on an output of the position sensor while the position sensor is aligned with the target position; storing a calibration file in a memory of the NDT instrument 2, the calibration file containing calibration data which is a function of structural data representing a three-dimensional structure of the test object in an area containing the target position; and calibrating the NDT instrument 2 using the calibration data in the calibration file.

The CAD model contains data about the airplane structure in the area of the inspection site, including information concerning one or more of the following: (a) material type (average attenuation, which will be determined through involved testing of many composite standards); (b) material thickness; (c) underlying structure (can be displayed on inspection instrument to help qualify odd signals); (d) presence of sealant (gain can be adjusted to account for reduced backwall signal); (e) presence of an EME layer; (f) average paint thickness; (g) fastener location (the user can be warned about odd signals if they are positioned directly over a fastener); and (h) the presence of repairs in the inspection area (if the CAD file has been kept up to date by the airline or other user). Such CAD model data can be used to generate a calibration file for the structure and provide the inspector with the situational awareness to make informed decisions about the inspection.

Figure 7:
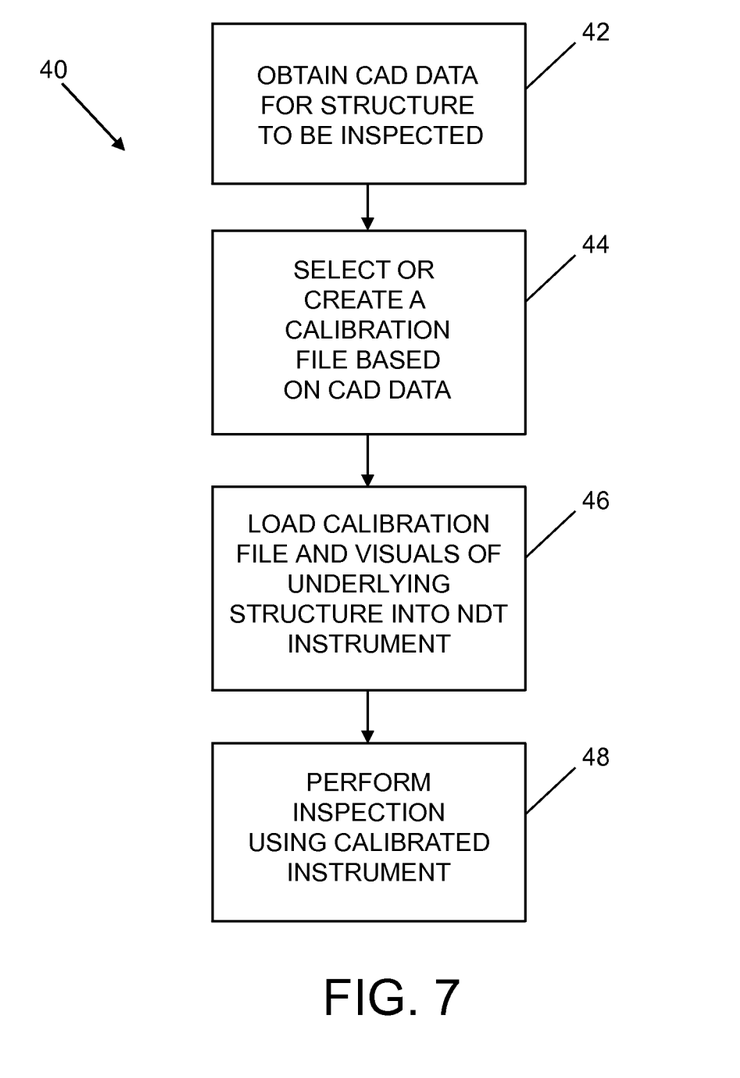
FIG. 7 is a flowchart identifying steps of a method for performing an inspection using an NDT instrument calibrated based on 3-D model data representing the part to be inspected.

The auto-calibration methods described may be incorporated in a method for non-destructive inspection of a portion of a manufactured part, such as an airplane. FIG. 7 is a flowchart identifying steps of a method 40 for performing an inspection using an NDT instrument calibrated based on 3-D model data representing the part or portion thereof to be inspected. First, CAD data for a structure to be inspected is obtained by a processor or computer (step 42). Then a calibration file is automatically created or selected based on that CAD data (step 44). That calibration file and associated visuals (i.e., display data) of the underlying structure to be inspected are then loaded into the NDT instrument 2 (step 46). The inspector is now ready to perform an inspection using the calibrated NDT instrument 2 (step 48).

Figure 8:
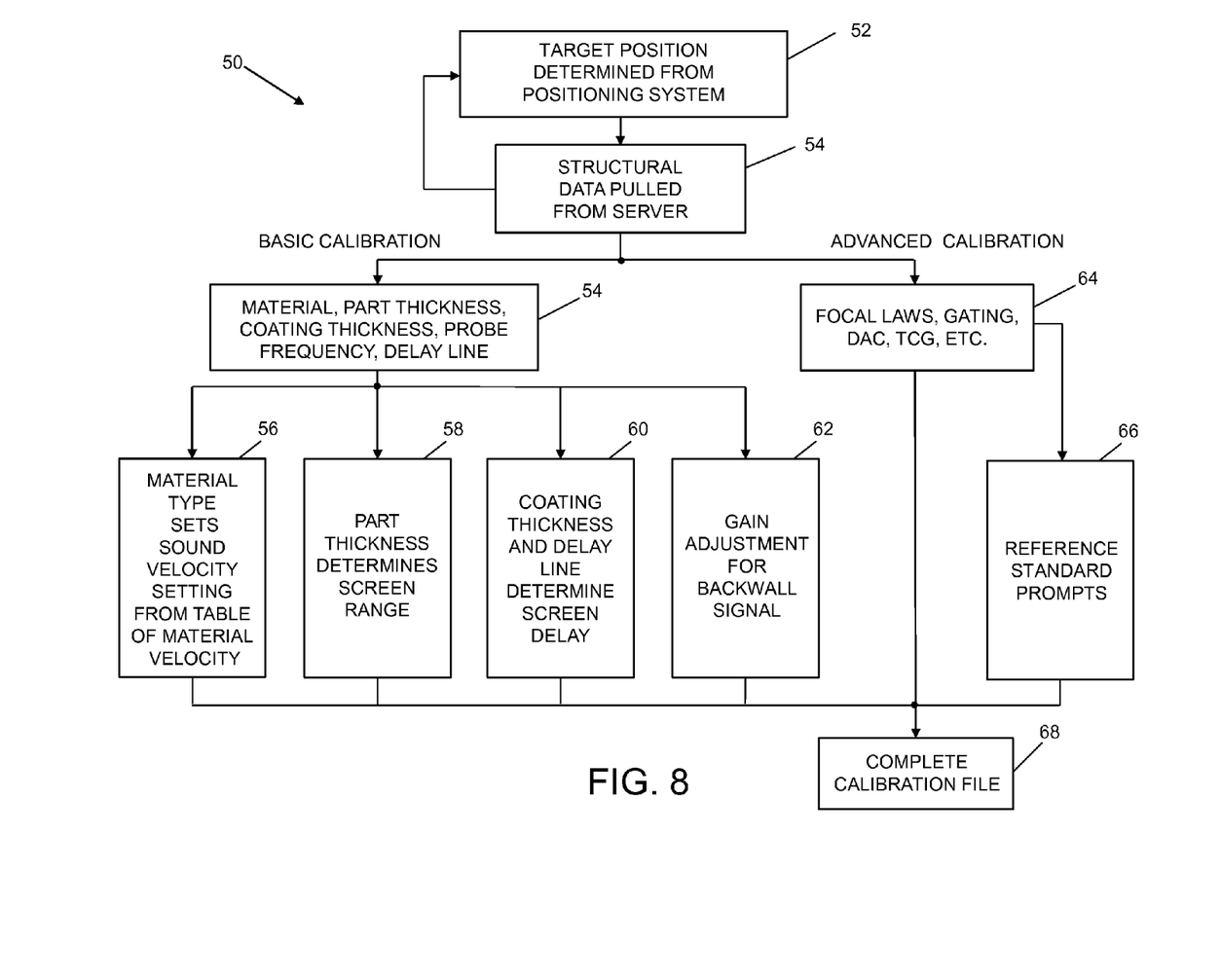
FIG. 8 is a flowchart identifying steps of a method 50 for generating a calibration file based on a target position on a surface of a test object, determined using a local positioning system, and associated structural data retrieved from a server.

FIG. 8 is a flowchart identifying steps of a method 50 for generating a calibration file using a local positioning system. First, the target position (i.e., the place on the surface of the test object where the underlying structure is to be inspected) is determined using the local positioning system (step 52). Then the structural data associated with that target position is pulled from a CAD model database server (step 54). The return arrow from block 54 to block 52 in FIG. 8 indicates a feature of an advanced embodiment that would allow for real-time updating of the target position and the calibration as the probe is moved across the part being inspected, which feature takes into account changes in thickness, material, etc. A simplified embodiment would involve pre-made procedures being attributed to certain areas on the airplane that are then loaded based on initial target position at the start of the inspection.

Still referring to FIG. 8, it can be seen that the structural data can be used to perform a basic calibration or an advanced calibration (which may include the basic calibration and additional calibration). In the basic calibration, calibration parameters such as material, part thickness, coating thickness, probe frequency, and delay line are selected based on the relevant structural data (step 54). The material type sets the sound velocity setting from a table of material velocities (step 56). The part thickness determines the screen range (step 58). The coating thickness and delay line determine the screen delay (step 60). In addition, the gain can be adjusted to take into account the backwall signal (step 62).

In accordance with an advanced calibration methodology, additional calibration parameters, such as focal laws, gating, Distance-Amplitude Correction (DAC), and Time-Compensated Gain (TCG), can be determined by a computer which is programmed with calibration software for processing the structural data (step 64). [In its simplest form DAC is a drawing on the ultrasound machine screen that accounts for the loss of sound over the sound path. TCG is a correction for the DAC curve that makes the curve a straight line by automatically adjusting the gain so that flaws of equal size over different sound paths (i.e., different depths) appear visually with the same screen level on the NDT instrument's screen.] Optionally, reference standard prompts can be automatically generated for more advanced calibrations operations (step 66). The inspector could be automatically prompted to a reference standard and given instructions at such times.

Finally, all of the calibration parameters are organized in accordance with a specified format to complete the calibration file (step 68). That calibration file is then used to calibrate the NDT instrument 2.

The use of CAD model data enables automation of a process that generally requires a trained NDT inspector. As a result, it removes a degree of human error from the calibration process. This cuts training costs and reduces inspection times by not requiring a trained NDT inspector to perform each and every inspection. Putting structural details in front of the inspector allows a more informed decision to be made about the inspection.

While apparatus and methods have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising at least one processing unit (e.g., a central processing unit, an integrated circuit or an arithmetic logic unit).

As used in the claims, the term "location" comprises position in a three-dimensional coordinate system and orientation relative to that coordinate system.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A method for non-destructive testing of an area of a test object containing a target position using a non-destructive testing instrument, comprising:
    storing three-dimensional model data in a computer-readable memory representing a three-dimensional model of a test object to be inspected, the three dimensional model being located in a test object coordinate system of the target object;
    displaying an image depicting a three-dimensional model of at least a portion of the test object as a graphical user interface on the display screen;
    manually selecting a target position on a surface of the target object using the graphical user interface;
    determining a first set of coordinates in the test object coordinate system of the test object, the first coordinates representing the selected target position on the surface of the test object;
    retrieving three-dimensional model data representing a three-dimensional structure of the test object in an area containing the target position from the computer-readable memory based on the first set of coordinates;
    generating a calibration file containing calibration parameter data which is a function of the retrieved three-dimensional model data;
    storing the calibration file in a memory of the non-destructive testing instrument;
    calibrating the non-destructive testing instrument using the calibration parameter data in the calibration file;
    using the calibrated non-destructive testing instrument to generate outgoing pulses that propagate toward the target position;
    using the calibrated non-destructive testing instrument to detect return pulses that propagate from the target position to the calibrated non-destructive testing instrument;
    using the calibrated non-destructive testing instrument to determine whether the detected return pulses are indicative of a presence of a structural anomaly or not at the target position; and
    activating a first visual indicator on the calibrated non-destructive testing instrument to indicate the presence of a structural anomaly at the target position if a determination is made that the detected return pulses indicate the presence of a structural anomaly or activating a second visual indicator on the calibrated non-destructive testing instrument to indicate the absence of a structural anomaly at the target position if a determination is made that the detected return pulses indicate the absence of a structural anomaly.

2. The method as recited in claim 1, wherein the calibration file is generated by the non-destructive testing instrument.

3. The method as recited in claim 1, wherein the calibration file is generated by a computer system, further comprising sending the calibration file to the non-destructive testing instrument.

4. The method as recited in claim 1, further comprising:
    sending a request for a calibration file to a calibration database server, the request for a calibration file being based on the target position and the retrieved three-dimensional model data; and
    receiving the calibration file from the calibration database server in response to sending of the request.

5. The method as recited in claim 1, further comprising:
    locating a local positioning system relative to the test object;
    generating a transformation matrix for transforming coordinates in a local positioning system coordinate system of the local positioning system into coordinates in the test object coordinate system of the test object; and
    determining a second set of coordinates representing the target position on the surface of the test object in the coordinate system of the local positioning system,
    wherein determining a first set of coordinates comprises transforming the second set of coordinates into the first set of coordinates using the transformation matrix.

6. The method as recited in claim 1, further comprising:
    attaching a position sensor to the non-destructive testing instrument; and
    moving the non-destructive testing instrument to a location at which the position sensor is aligned with the target position,
    wherein determining a first set of coordinates comprises calculating the first set of coordinates based on an output of the position sensor while the position sensor is aligned with the target position.

7. The method as recited in claim 1, wherein the retrieved three-dimensional model data comprises information concerning one or more of the following structural features of the test object at or in the area containing the target position: physical dimensions, material characteristics, fastener locations, structural anomalies, average paint thickness, hidden stringers, and electromagnetic effects protection layers.

8. The method as recited in claim 1, wherein the retrieved three-dimensional model data comprises data characterizing an alteration or a repair to the test object in the area containing the target position.

9. A method for non-destructive testing of an area of a test object containing a target position using a non-destructive testing instrument, comprising:
    storing three-dimensional model data in a computer-readable memory representing a three-dimensional model of a test object to be inspected, the three dimensional model being located in a test object coordinate system of the target object;
    displaying an image depicting a three-dimensional model of at least a portion of the test object as a graphical user interface on the display screen;
    manually selecting a target position on a surface of the target object using the graphical user interface;

determining a first set of coordinates in the test object coordinate system of the test object, the first coordinates representing the selected target position on the surface of the test object;

retrieving three-dimensional model data representing a three-dimensional structure of the test object in an area containing the target position from the computer-readable memory based on the first set of coordinates;

generating a calibration file containing calibration parameter data which is a function of the retrieved three-dimensional model data;

calibrating the non-destructive testing instrument using the calibration parameter data in the calibration file;

using the calibrated non-destructive testing instrument to generate outgoing pulses that propagate toward the target position;

using the calibrated non-destructive testing instrument to detect return pulses that propagate from the target position to the calibrated non-destructive testing instrument;

using the calibrated non-destructive testing instrument to determine whether the detected return pulses are indicative of a presence of a structural anomaly or not at the target position; and activating a first visual indicator on the calibrated non-destructive testing instrument to indicate the presence of a structural anomaly at the target position if a determination is made that the detected return pulses indicate the presence of a structural anomaly or activating a second visual indicator on the calibrated non-destructive testing instrument to indicate the absence of a structural anomaly at the target position if a determination is made that the detected return pulses indicate the absence of a structural anomaly.

10. The method as recited in claim 9, further comprising:

locating a local positioning system relative to the test object;

generating a transformation matrix for transforming coordinates in a local positioning system coordinate system of the local positioning system into coordinates in the test object coordinate system of the test object; and determining a second set of coordinates representing the target position on the surface of the test object in the coordinate system of the local positioning system, wherein determining a first set of coordinates comprises transforming the second set of coordinates into the first set of coordinates using the transformation matrix.

11. The method as recited in claim 9, wherein the retrieved three-dimensional model data comprises information concerning one or more of the following structural features of the test object at or in the area containing the target position: physical dimensions, material characteristics, fastener locations, structural anomalies, average paint thickness, hidden stringers, and electromagnetic effects protection layers.

12. The method as recited in claim 9, wherein the retrieved three-dimensional model data comprises data characterizing an alteration or a repair to the test object in the area containing the target position.

13. A method for non-destructive testing of an area of a test object containing a target position using a non-destructive testing instrument, comprising:

storing three-dimensional model data in a computer-readable memory representing a three-dimensional model of a test object to be inspected located in a test object coordinate system of the target object;

locating a local positioning system coordinate system of a local positioning system relative to the test object coordinate system of a test object;

locating a feature on the test object relative to the local positioning system coordinate system;

converting the location of the feature in the local positioning system coordinate system to a location of the feature in the test object coordinate system;

displaying an image depicting a three-dimensional model of at least a portion of the test object as a graphical user interface on the display screen;

manually selecting a target position on a surface of the target object using the graphical user interface;

retrieving three-dimensional model data representing a three-dimensional structure of the test object in an area containing the target position from the computer-readable memory;

generating a calibration file containing calibration parameter data which is a function of the retrieved three-dimensional model data;

storing the calibration file in a memory of the non-destructive testing instrument;

calibrating the non-destructive testing instrument using data in the stored calibration file;

using the calibrated non-destructive testing instrument to generate outgoing pulses that propagate toward the target position;

using the calibrated non-destructive testing instrument to detect return pulses that propagate from the target position to the calibrated non-destructive testing instrument;

using the calibrated non-destructive testing instrument to determine whether the detected return pulses are indicative of a presence of a structural anomaly or not at the target position; and activating a first visual indicator on the calibrated non-destructive testing instrument to indicate the presence of a structural anomaly at the target position if a determination is made that the detected return pulses indicate the presence of a structural anomaly or activating a second visual indicator on the calibrated non-destructive testing instrument to indicate the absence of a structural anomaly at the target position if a determination is made that the detected return pulses indicate the absence of a structural anomaly.

14. The method as recited in claim 13, wherein the retrieved three-dimensional model structural data comprises information concerning one or more of the following structural features of the test object at or in the area containing the target position: physical dimensions, material characteristics, fastener locations, structural anomalies, average paint thickness, hidden stringers, and electromagnetic effects protection layers.

15. The method as recited in claim 13, wherein the retrieved three-dimensional model structural data comprises data characterizing an alteration or a repair to the test object in the area containing the target position.

* * * * *